(12) United States Patent
Tulkki

(10) Patent No.: US 6,409,677 B1
(45) Date of Patent: Jun. 25, 2002

(54) METHOD FOR TEMPERATURE COMPENSATION IN A COMBINED PRESSURE AND TEMPERATURE SENSOR

(75) Inventor: Sauli Tulkki, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 0 days.

(21) Appl. No.: 09/577,663

(22) Filed: May 25, 2000

Related U.S. Application Data
(60) Provisional application No. 60/136,401, filed on May 27, 1999.

(51) Int. Cl.⁷ .................................................. A61B 5/00
(52) U.S. Cl. ...................................... 600/561; 600/549
(58) Field of Search .................................. 600/486, 488, 600/549, 561, 587; 73/54.43, 61.46, 61.97

(56) References Cited

U.S. PATENT DOCUMENTS

| | | | | |
|---|---|---|---|---|
| 4,554,927 A | | 11/1985 | Fussell ..................... 128/670 |
| 4,766,655 A | * | 8/1988 | Hickox ..................... 29/25.35 |
| 5,269,311 A | | 12/1993 | Kirchner et al. ............ 128/672 |
| 5,535,752 A | * | 7/1996 | Halperin et al. ............ 600/483 |
| 5,551,301 A | * | 9/1996 | Cowan ....................... 73/708 |
| 5,715,827 A | | 2/1998 | Corl et al. .................. 128/673 |

FOREIGN PATENT DOCUMENTS

WO      97/27802      8/1997

OTHER PUBLICATIONS

Collins et al., "Pressure Sensor Electronic Converter," IBM Technical Disclosure Bulletin, vol. 9, No. 3 (Aug. 1966), pp. 333–334.

* cited by examiner

*Primary Examiner*—Kevin Shaver
*Assistant Examiner*—Pamela Wingood
(74) *Attorney, Agent, or Firm*—Foley & Lardner

(57) ABSTRACT

A method for temperature compensation is disclosed which comprises the excitation of sensors in a guide wire sensor assembly so as to produce two distinguishable signals. At least a component of at least one of the signals is representative of the cable resistance and can be used for compensation purposes. There is also provided an apparatus suitable for such measurements having temperature compensation circuitry. The compensation circuitry comprises circuitry for selectively and independently registering a resistance value for a passive resistor on the chip.

26 Claims, 9 Drawing Sheets

METHOD FOR TEMPERATURE COMPENSATION IN A COMBINED PRESSURE AND TEMPERATURE SENSOR

The Applicant hereby claims the benefit of U.S. provisional application 60/136,401, filed May 27, 1999. The entire contents of this provisional application are incorporated herein by reference.

The present invention relates generally to a method of determining the pressure, temperature and optionally flow in the medical area, especially to in situ measurement of the intracoronary pressure, distally of a stricture using a guide wire having a pressure sensor at its distal end.

BACKGROUND OF THE INVENTION

In order to determine and investigate the ability of a specific coronary vessel to supply blood to a heart muscle, i.e. the myocardium, there is a method through which the intracoronary pressure distally and proximal of a stricture are measured. In the method the so called Fractional Flow Reserve (see "Fractional Flow Reserve" Circulation, vol. 92, No 11, Dec. 1, 1995, by Nico H. J. Pijls et al.) is used. Briefly $FFR_{myo}$ is defined as the ratio between the pressure distally of a stricture and the pressure proximal of a stricture, i.e. $FFR_{myo}=P_{dist}/P_{prox}$. The measurement of the distal pressure is made in the vessel using a micro-pressure transducer, and the proximal pressure is the arterial pressure.

In WO 97/27802 there is disclosed a sensor for temperature and pressure measurements having a pressure sensitive resistor (referred to as an active resistor) and a temperature sensitive resistor (referred to as a passive resistor). These resistors are part of a Wheatstone bridge comprising a total of four resistors and three "parasitic" cable resistances. Two different measurements are performed in this bridge, namely a measurement of a differential output voltage (potential difference between the active and passive circuit) which is used for pressure measurement and single ended output voltage (voltage across the passive circuit), which is used for temperature measurement. Only the passive and the active resistor are located on the actual sensor chip that is inserted into the body. The remaining resistors in the bridge are located externally, suitably in the control unit, and are coupled to the chip via electrical leads running inside a guide wire on the distal end of which the chip is located. This system functions appropriately when the environment is such that the properties of the electrical leads are not affected. However, in view of the fact that the leads have extremely small dimensions and are relatively long, the resistance of the leads could vary considerably if the fraction of the length leads that are exposed to the body temperature varies, namely, if the guide wire needs to be manipulated over distances of more than a few centimeters. This effect is obtained in general when the temperature surrounding the guide wire changes e.g. when flushing with saline having a temperature differing the from body temperature. These effects will have an impact on the temperature and pressure signals, and should be compensated for. In particular the read-out value of the temperature sensor (the passive resistor), which is also used for temperature compensation, will be incorrect. Thus, it is desirable to obtain a correct temperature read-out. One way of achieving this would be to provide separate leads coupled so as to enable a direct reading of the voltage drop across the passive (temperature sensitive) resistor. However, this would require the provision of five electrical leads inside the guide wire, and there is simply not space enough to make this possible.

In U.S. Pat. No. 5,715,827 (Cardiometrics), which is incorporated in its entirety herein, there is disclosed apparatus for pressure measurements using two resistors provided on a flexible diaphragm. The resistors are mounted so as to have opposite response to pressure, i.e. one resistor gives a positive signal and the other a negative. In the patent it is stated that this arrangement provides a temperature compensation for the signal. However, this arrangement has the same inherent problem with cable resistances affecting the signal.

SUMMARY OF THE INVENTION

The object of the invention is therefore to provide a measurement method using a single unit having as few electrical leads as possible, namely only three, and allowing compensation for variations in resistance of the leads coupling the resistors in the sensor to the control unit, in order to obtain a reliable measurement.

The object outlined above is achieved according to the invention with the method of measurement described herein. The method comprises the excitation of the sensors so as to produce two distinguishable signals. At least a component of at least one of the signals is representative of the cable resistance and can be used for compensation purposes.

In a second aspect of the invention there is provided an apparatus suitable for such measurements having temperature compensation means. The compensation means comprises circuitry for selectively and independently registering a resistance value for the passive resistor on the chip.

Further scope of application will become apparent from the detailed description given hereinafter.

Nevertheless, it should be understood that the detailed description and specific examples, while describing a measurement method, are given as an illustration only. Various changes and modifications within the spirit and scope of the invention will become apparent to those skilled in the art from this detailed description.

BRIEF DESCRIPTION OF THE DRAWINGS

The present invention will become more fully understood from the detailed description given herein below and accompanying drawings that are given as an illustration only, therefore the above description does not present any limitation to the invention at hand and herein.

DETAILED DESCRIPTION OF THE SYSTEM AND THE METHOD OF MEASUREMENT

Figure 1A:
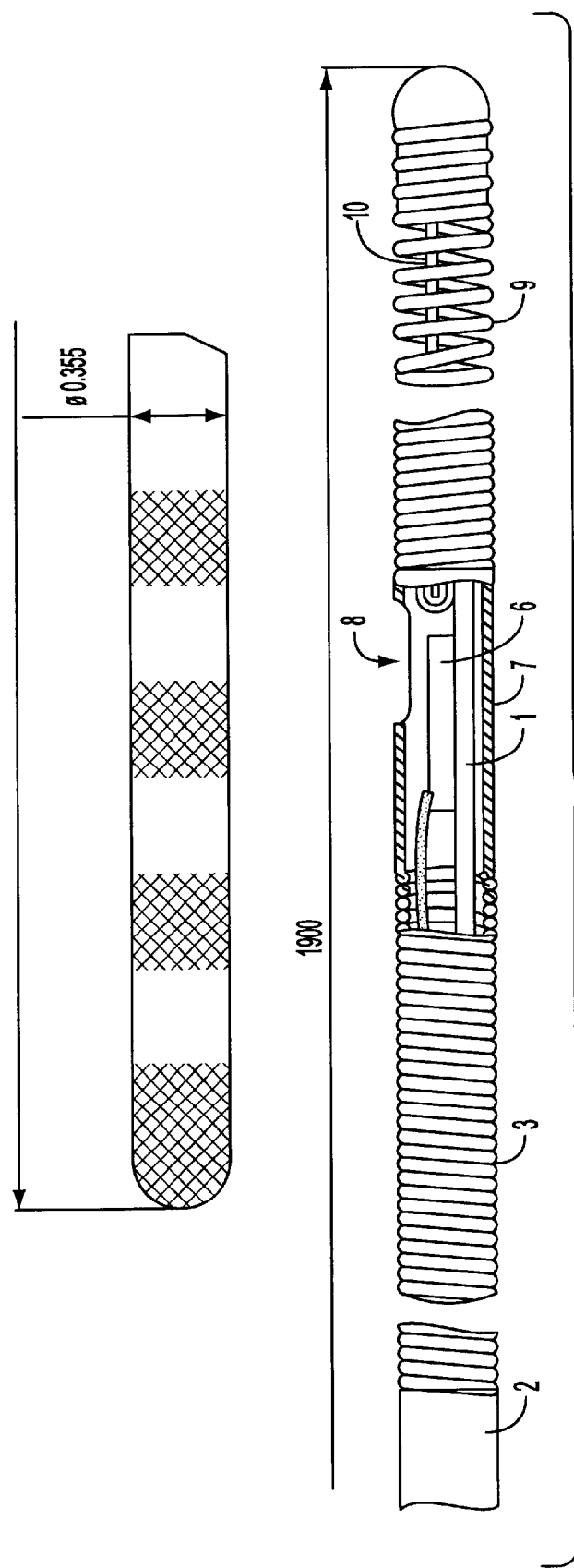
FIG. 1a shows a sensor/guide wire assembly to be used together with the invention.

A distal portion of a sensor and guide wire assembly as disclosed in WO 97/27802, is shown in FIG. 1a. The device comprises a solid wire 1 inserted into a proximal tube portion 2. The wire 1 forms the distal portion of the guide wire and is extended beyond the distal end of the proximal tube 2 where the tube is connected to, or provided with an integrally formed, spiral portion 3. At the distal end of the wire 1, a pressure sensor 6 is mounted. Between the wire 1 and the spiral portion 3, electrical leads from the electrical circuitry run parallel with the wire 1. The sensor 6 is protected by a short section of a tube 7 having an aperture 8 through which a surrounding medium acts on the pressure sensor. At the very distal end of the device there is a radio opaque coil 9 made of Pt and used for location purpose. There is also provided a safety wire 10 for securing the distal part or the spiral 9.

The proximal tube 2 and the spiral portion 3 may be connected in such a way that they can be used as an electrical shield.

Figure 1B:
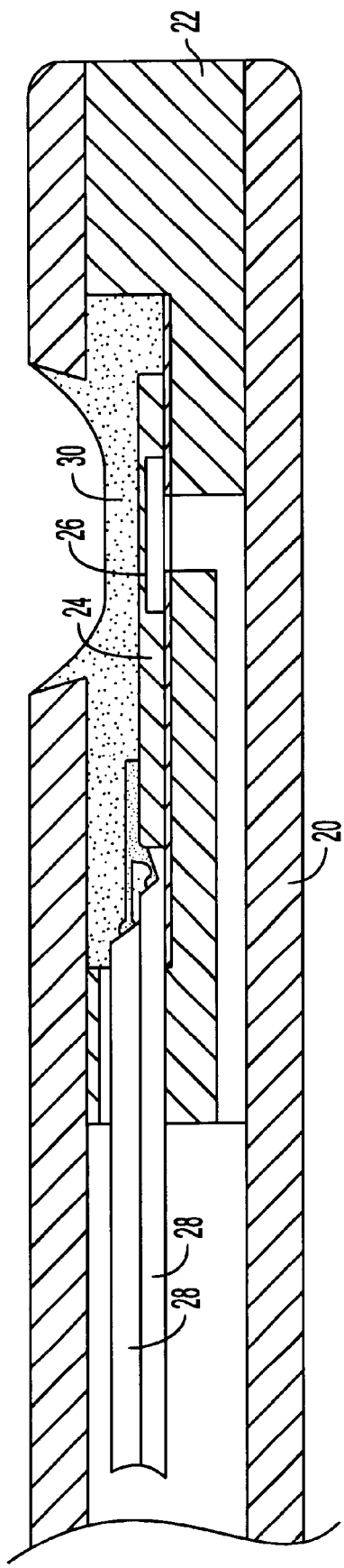
FIG. 1b shows a distal tip of a catheter where a sensor is mounted and together with which the invention is to be used.
Figure 2:
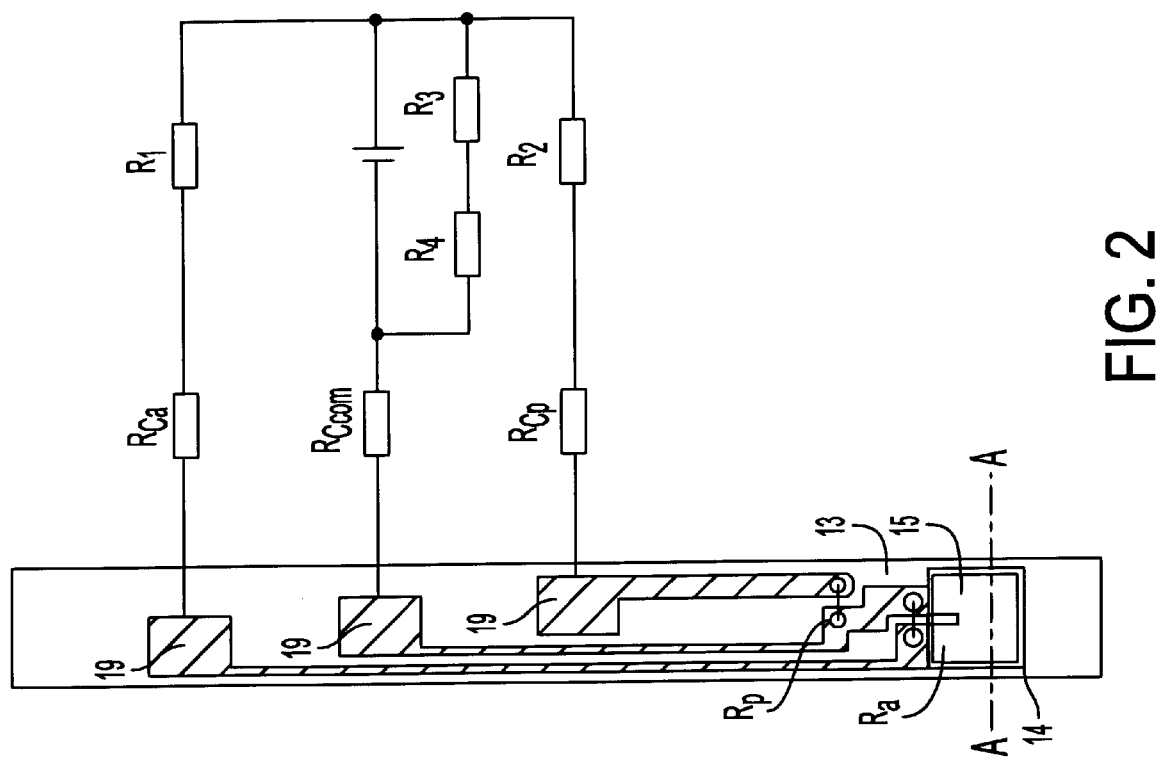
FIG. 2 is a schematic top view of a sensor chip and the resistances in the system.

In FIG. 1b there is shown a catheter tip pressure transducer which can be used with the present invention. This system comprises a catheter 20 closed by an end member 22. This member also functions as a support for a sensor 24 having a pressure sensitive diaphragm 26. Electrical leads 28 couple the sensor to external equipment. The sensor may be protected by a material such as silicon rubber 30.

The prior art measurement system disclosed in WO 97/27802 will now be described with reference to FIG. 3.

Pressure sensing resistor $R_a$ (a for "active") and temperature sensing resistor $R_p$ (p for "passive") are located on the actual sensor chip, and are coupled to the measurement device using insulated cables having resistances $R_{ca}$ $R_{cp}$ and $R_{com}$, these cables are mounted inside said proximal tube. These cables couple resistors $R_a$, $R_p$ into the measurement device, and together with internal resistors $R_1$ and $R_2$ they form a Wheatstone bridge. This Wheatstone bridge is driven by the excitation voltage $V_{DCE}$, and the differential output voltage $V_{(a-p)}$ from the bridge is read using an instrumentation amplifier. Single ended output voltage $V_p$ in the temperature sensing circuit is read by another instrumentation amplifier. Amplifier output signals $V_{(a-p)}$ and $V_p$ are coupled into a multiplexer, the amplifier outputs $V_{(a-p)}$ and $V_p$ being sequentially switched into an A/D converter for conversion into digital data. This data is read from the A/D converter using a microcontroller CPU or digital signal processor DSP. CPU/DSP performs calculations needed to obtain the final pressure or temperature signal, and finally the measured values are presented on a numerical display.

The prior art measurement method will now be described with reference to FIG. 3.

$R_a$ and $R_a$ are the active sensor element and the resistance of the passive element respectively, as previously described. Their resistance may vary differently with the temperature i.e. $TC_{Ra} \neq TC_{Rp}$. Therefore a compensation of the pressure signal has to be made to compensate for the error related to varying temperature, i.e. it is known from the calibration curve which is achieved during the manufacturing process how much has to be added to or subtracted from the registered pressure signal in order to get a correct pressure value.

Figure 3:
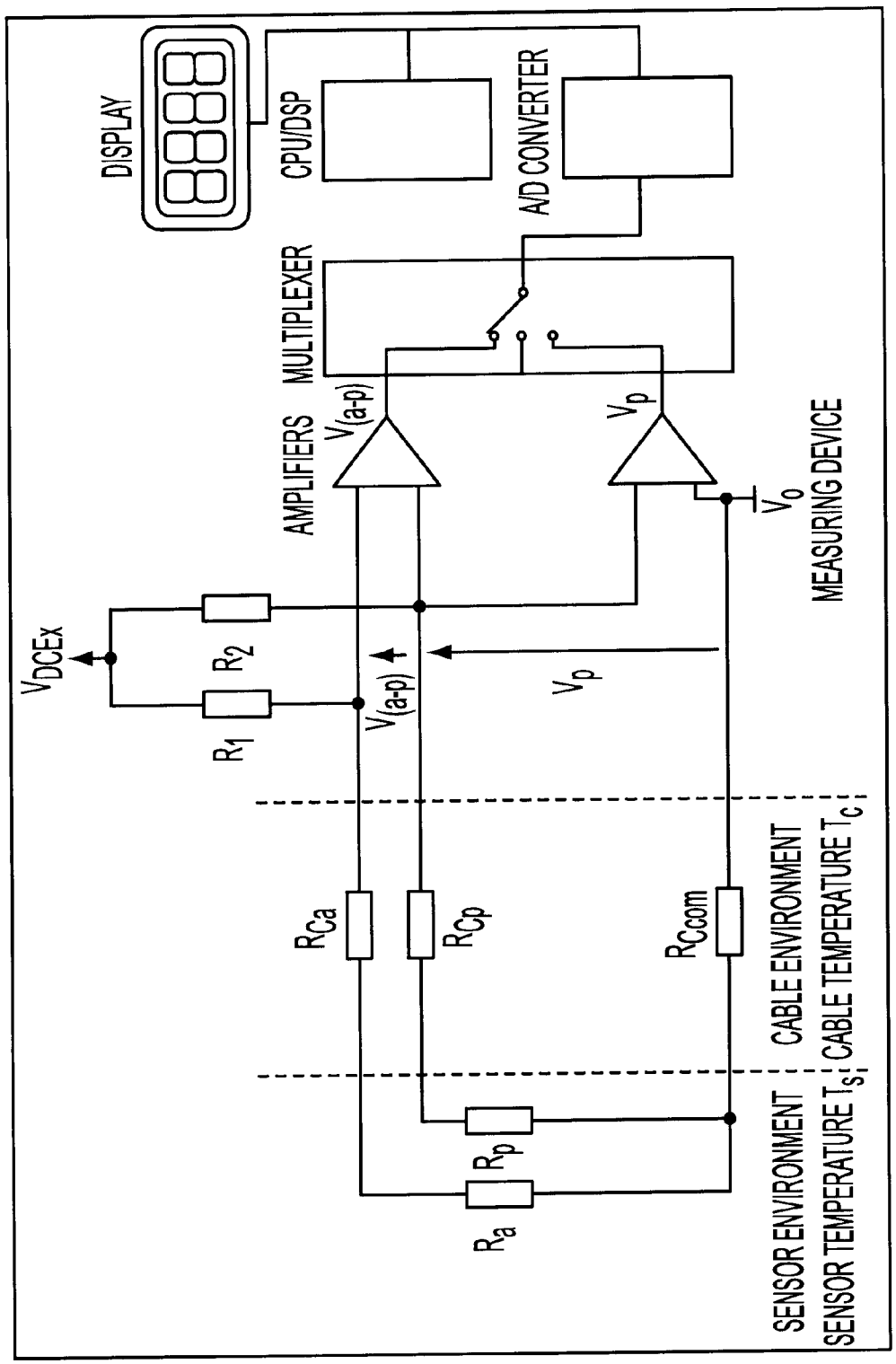
FIG. 3 is a simplified schematic circuit of the system used, without the inventive feature.

During pressure measurement the circuit disclosed in FIG. 3 is supplied with excitation voltage or current (DC or AC). At present most systems of the type the present invention is concerned with are operated with excitation voltages of up to 15 V. However, it is conceivable to operate at substantially higher voltages, provided the components of the system are designed accordingly. The differential voltage of the active and the passive circuits $V_{(a-p)}$ is a representative signal for the measured pressure, and single ended voltage $V_p$ is a representative signal for the measured temperature. Because of the fact that the resistors $R_a$ and $R_p$ are not identical in terms of their temperature dependence, the differential voltage $V_{(a-p)}$ will be temperature dependent, therefore the pressure signal $V_{(a-p)}$ to be compensated against varying temperature. During the manufacturing process every sensor is characterised in terms of temperature dependence and the calibration parameter is achieved by measuring simultaneously the temperature coefficient $TC_{Rp}$ of the passive element and the difference between $TC_{Rp}$ and temperature coefficient $TC_{Ra}$ of the active sensing element (this is done during the manufacturing process). The result is thus a compensation factor $$T_{Factor} = \frac{TC_{Ra} - TC_{Rp}}{TC_{Rp}} \quad (1.0)$$

which is used to compensate the sensor signal for temperature variations. This factor which is unique to each individual sensor, is preferably stored in a PROM or the like, attached to the assembly of which the sensor forms a part. The compensated sensor signal is then equal to $$V_{a-p} - T_{Factor} * V_p \quad (1)$$

where, $V_{a-p}$ and $V_p$ are the measured potential difference between the active and the passive circuit, and the measured potential drop across the passive circuit, respectively (see FIG. 3).

However, as indicated previously, this method has a drawback which has to do with the potential $V_p$ being dependent on changes of the cable resistance as well, (i.e. $R_{Cp}$ and $R_{Ccom}$), such that $$V_p = V_{Ex} \frac{R_{Cp} + R_P + 2R_{Ccom}}{R_{Cp} + R_P + 2R_{Ccom} + R_2} \quad (1.2)$$

where, $V_{Ex}$ is the excitation voltage of the bridge (this is a simplification under the previously made assumptions).

The prior art measurement method will function satisfactorily provided that the signal produced by change in the resistances of the cable, i.e. $R_{Cp}$, $R_{Ca}$ and $R_{Ccom}$ due to the temperature, is negligible compared to the measured temperature signal. However, when e.g. small dimensions are needed the resistance per unit length becomes high, which results in substantial total resistance of the cable. In order to illustrate this effect the following example is given. The cables used in the above mentioned International Patent Application WO 97/27802 have a diameter 0.050 mm, length 1750 mm, resistance ≈40 ohm. The temperature coefficient of copper is ≈0.00433° C.$^{-1}$, which results in an increase of resistance in the cable by 0.173 ohm/° C. The effective influence of this resistance change in the passive circuit used for temperature measurement is three times higher because of the fact that the total length of cable in the circuit is 2 * 1750 mm ($R_{Cp}+R_{Ccom}$) and the fact that current passing through the common cable $R_{Ccom}$ is a sum of currents in the passive and active circuit, and thus the effective influence of the cable can now be defined as 0.520 ohm/° C. Now, the temperature difference between the room temperature and the body temperature is approximately 17° C. resulting in the resistance change of 8.33 ohm if the whole cable length is moved from room temperature into body temperature. This shall be compared with the fact that the temperature coefficient of the passive resistor $R_p$ located on the sensor chip is typically ≈0.000300° C.$^{-1}$. The resistance of the named resistor is typically ≈3000 ohm, which results in the desired temperature signal of 0.9 ohm/° C. The relationship between undesired change in the cable resistance and desired temperature signal can now be calculated as 0.52/0.9≈60%, which means that 37% of the temperature signal can actually originate from the change in cable temperature. This fact is crucial especially when the sensor is used for the temperature measurements, and the temperature compensation of the pressure measurements is also influenced. Namely, there are applications where the cable length, which is exposed to the temperature change during the measurement is almost impossible to predict prior to the measurement procedure. The parts of the cable that will undergo a resistance change are those that are present in the same environment as the active sensor element (i.e. exposed to body temperature, higher than ambient). The contribution to the signal from the change of the cable resistances will thus be dependent on that length. In case the length affected by the temperature change is large, the contribution will also be large. Thus, a compensation for the change of the cable resistance is necessary.

In another prior art measurement method and system disclosed in the above mentioned U.S. Pat. No. 5,715,827 there are provided two "active" resistors, coupled in a first and a second branch of a Wheatstone bridge respectively. In this system the resistors have opposite response to pressure, such that one of the resistors responds positively to pressure changes and the other responds negatively to a pressure change. However, the basic inherent problem with "parasitic" cable or lead substances is the same as for the above depossed system. The present invention is equally well applicable to the later system without inventive skills being required.

Figure 4:
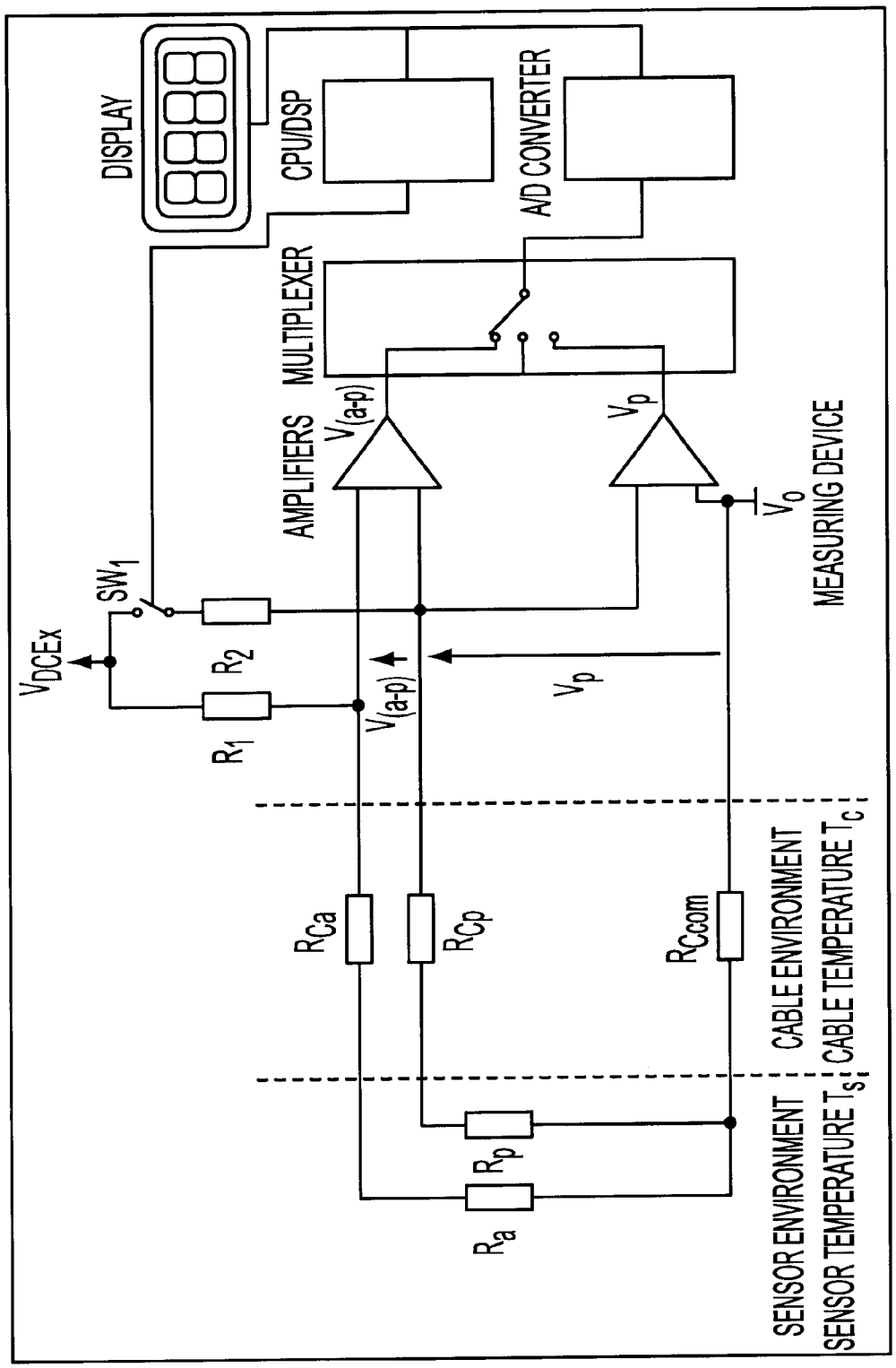
FIG. 4 is a simplified schematic circuit of the system used, with a first embodiment of the inventive feature.

Now a first embodiment of the apparatus according to the invention will be described with reference to FIG. 4.

Basically the same set up as in the prior art measurement system is used. However, there is the additional provision of means for providing two in time differing "modes" of excitation, which are generated by a switch $SW_1$.

Switch $SW_1$ is coupled between $V_{DCEx}$ and $R_2$ in order to cut the excitation voltage to the passive circuit. If a measurement is now carried out with $SW_1$ open, and if one assumes that the sum of $R_p$ and $R_{Cp}$ is negligible compared to the input impedance of the amplifiers that measure the voltages $V_p$ and $V_{a-p}$, $V_p$ will then be a measure of potential drops across $R_{Ccom}$ (no current is flowing in the passive circuit), i.e. the contribution to the measured temperature signal from the change of the cable resistances due to the temperature. Now that the contribution to the temperature signal from the change of the cable resistances is determined it is possible to obtain the compensated temperature signal. It is given by $$V_p - 3*V_{Popen} \qquad (1.4)$$

where, $3*V_{P\ open}$ is the compensation for the change of the cable resistances and $V_{Popen}$ is the voltage measured across the passive circuit with $SW_1$ open.

When $SW_1$ is closed the active element of the sensor yields a signal representative of the pressure, and its value is given by the signal $V_{a-p}$. The switch $SW_1$ is operable at a selected frequency, the magnitude of which is dependent on other system parameters, and could vary within wide limits.

Now a second embodiment of the apparatus according to the invention will be described with reference to FIGS. 5–6.

Another way of obtaining compensation for the cable resistance to create two different modes of excitation using two different excitation voltages separated from each other in frequency. A schematic illustration is shown in FIG. 5.

In this embodiment the Wheatstone bridge is driven by the excitation voltage $V_{ACEx}$ which is common to active and passive circuit. There is also a second excitation mode implemented, in this example a DC-voltage. It could of course be an AC voltage of a different frequency or phase. This additional DC excitation is applied in the active circuit. Now there are three signals or components of signals which are of interest in this application, the AC-component of the differential voltage $V_{(a-p)}$ referred to as $V_{(a-p)AC}$ in FIG. 5, which is a measure of the pressure, the AC-component of the single ended voltage $V_p$ in FIG. 5 referred to as $V_{pAC}$, which is a measure of the temperature, and finally a DC-component of the single ended voltage $V_p$ in FIG. 5 referred to as $V_{pDC}$, which is proportional to the resistance in the common cable $R_{Ccom}$.

In order to obtain the different components of the differential voltage $V_{(a-p)}$ and the single ended voltage $V_p$ it becomes necessary to employ filtering functions.

The AC-component of the differential voltage $V_{(a-p)}$ is obtained by high-pass filtering the signal before entering into the amplifier. The output from this amplifier is then fed into the multiplexer and further to the A/D converter where the signal is converted into the digital code. This digital code is read by CPU/DSP which also calculates e.g. the RMS (root mean square) value of the pressure signal.

The AC-component of the single ended voltage $V_p$ is obtained by high-pass filtering the signal before entering into the amplifier. The output from this amplifier is then fed into the multiplexer and further to the A/D converter where the signal is converted into the digital code. This digital code is read by CPU/DSP which also calculates e.g. the RMS (root mean square) value of the temperature signal.

An additional amplifier is introduced to obtain the DC-component of the single ended voltage $V_p$ which is low-pass filtered before entering said amplifier. The output from this amplifier is then fed into the multiplexer and further to the A/D converter where the signal is converted into the digital code, this digital code is read by CPU/DSP.

It is reasonable to assume that the internal impedance of the AC excitation source is near zero. Under this assumption we can draw the equivalent circuit for calculation of the $R_{Ccom}$ which is shown in the FIG. 6.

In order to simplify the algorithm we can assume that $R_{Ccom} = R_{Cp} = R_{Ca} << R_1 = R_2 = R_a = R_p$.

Now we will be able to calculate the resistance in the common cable. It is given by $$2*V_{pDC}*(R_1+R_a)/(V_{DCEx}-2*V_{pDC})$$

It is also possible to obtain the compensated temperature signal. It is given by $$V_{pAC} - 3V_{pDC}$$

Now an alternative implementation of the second embodiment of the invention will be described with reference to FIG. 7.

Figure 7:
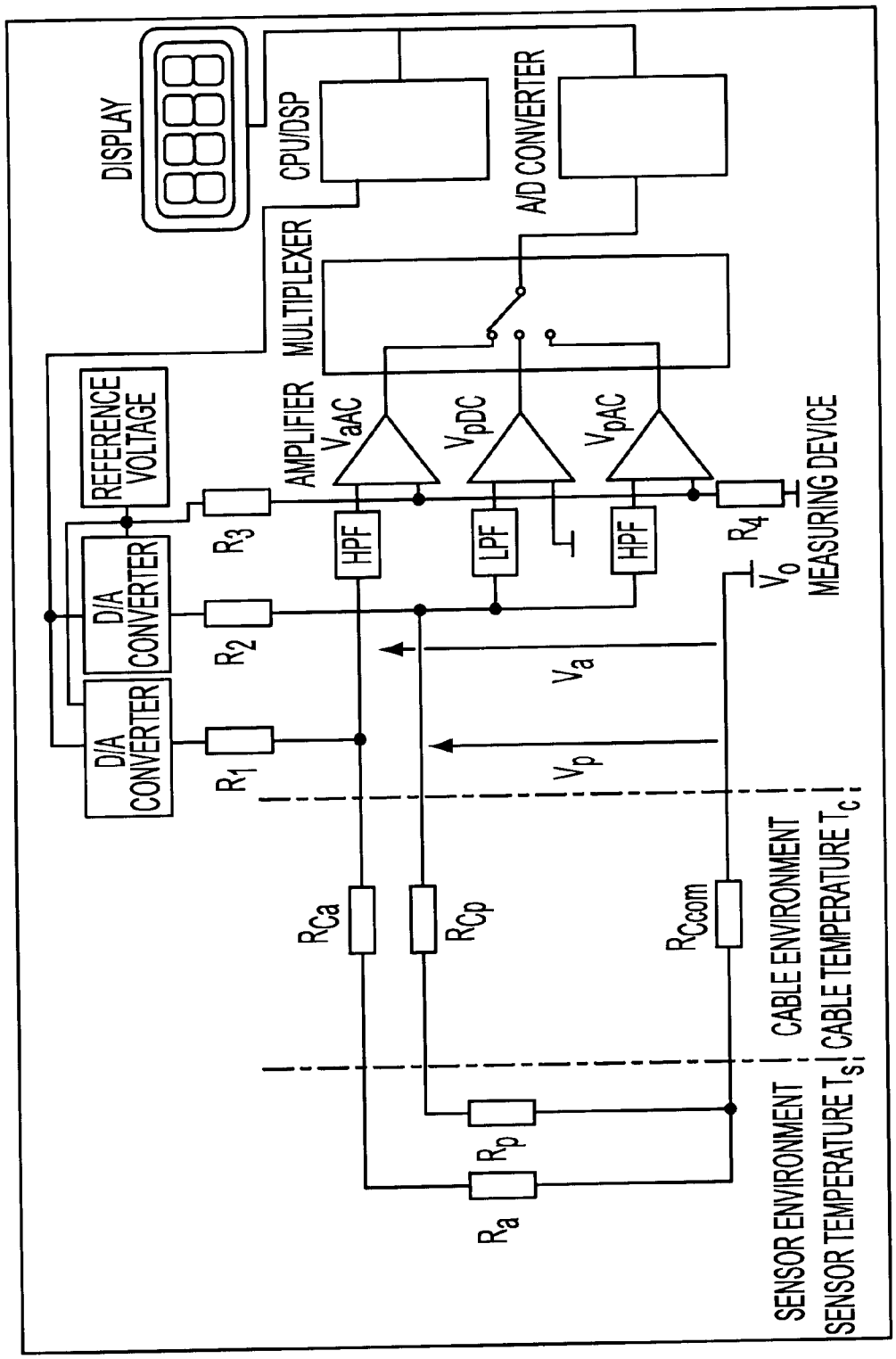
FIG. 7 is a simplified schematic circuit showing an alternative configuration of the measurement system with the inventive feature.

The control unit shown in FIG. 7, comprises a first and a second instrumental amplifier having inputs for receiving the pressure signal and the temperature signal respectively, and outputs delivering a processable out-signal. It comprises a multiplexer coupled to the outputs of the amplifiers, an A/D converter coupled to the multiplexer, and a control unit coupled to sequentially receive outputs from the A/D converter.

It is provided with excitation circuitry comprising a DC voltage source and an AC voltage source, whereby the DC and AC excitation voltages are superimposed on each other.

The control unit further comprises a high pass filter coupled to the input of the first instrumental amplifier, the input being coupled so as to receive a high frequency component of the pressure signal. The second instrumental amplifier has a low pass filter coupled to its input, the input being coupled so as to receive a low frequency component of the temperature signal. A third instrumental amplifier has a high pass filter coupled to its input, the input being coupled so as to receive a high frequency component of the temperature signal and an outputs delivering a processable out-signal. Furthermore there is the multiplexer coupled to the outputs of the amplifiers, the A/D converter coupled to the multiplexer, and the control unit coupled to sequentially receive outputs from the A/D converter.

In this alternative implementation, the Wheatstone bridge is driven by two D/A converters controlled from the CPU/DSP unit. There is also a reference voltage source which is used for the setting of the full scale output from the D/A converters. This reference is also fed into the voltage divider network containing resistors $R_3$ and $R_4$, the middle point voltage from this divider is used as a reference level for the input amplifiers measuring $V_{aAc}$ and $V_{pAC}$, this makes it possible to use higher gain without saturating these amplifiers.

Two excitation modes can now be produced by supplying the D/A converters with samples of data, i.e. the D/A converter supplying the circuit containing $R_1$ $R_{Ca}$ and $R_a$ is fed with samples containing the waveform used as common excitation superimposed on the DC level used as the second excitation mode, the D/A converter supplying the circuit containing $R_2$, $R_{Cp}$ and $R_p$ is fed with samples containing only the waveform used as the common excitation.

Now there are three signals or components of signals which are of interest in this application, the AC-component of the single ended voltage $V_a$ referred to as $V_{aAC}$ in FIG. 7, the AC-component of the single ended voltage $V_p$ (in FIG. 7 referred to as $V_{pAC}$), which is a measure of the temperature, the pressure is calculated as a difference between $V_{aAC}$ and $V_{pAC}$ and finally the DC-component of the single ended voltage $V_p$ (in FIG. 7 referred to as $V_{pDC}$), which is proportional to the resistance in the common cable $R_{Ccom}$.

In order to obtain the different components of the voltages $V_a$ and $V_p$ it becomes necessary to implement filtering functions.

In this implementation the AC-component of the single ended voltage $V_a$ is obtained by high-pass filtering the signal before feeding it into the amplifier. The output from this amplifier is then fed into the multiplexer and further to the A/D converter where the signal is converted into the digital data. The digital data is read by the CPU/DSP which calculates e.g. the RMS (root mean square) value of the signal.

The AC-component of the single ended voltage $V_p$ is obtained by high-pass filtering the signal before entering into the amplifier. The output from this amplifier is then fed into the multiplexer and further to the A/D converter where the signal is converted into the digital data. This digital data is read by the CPU/DSP which also calculates e.g. the RMS (root mean square) value of the temperature signal.

An additional amplifier is introduced to obtain the DC-component of the single ended voltage $V_p$ which is also low-pass filtered before entering its amplifier. The output from this amplifier is then fed into the multiplexer and further to the A/D converter where the signal is converted into the digital data, this digital data is read by the CPU/DSP.

Figure 5:
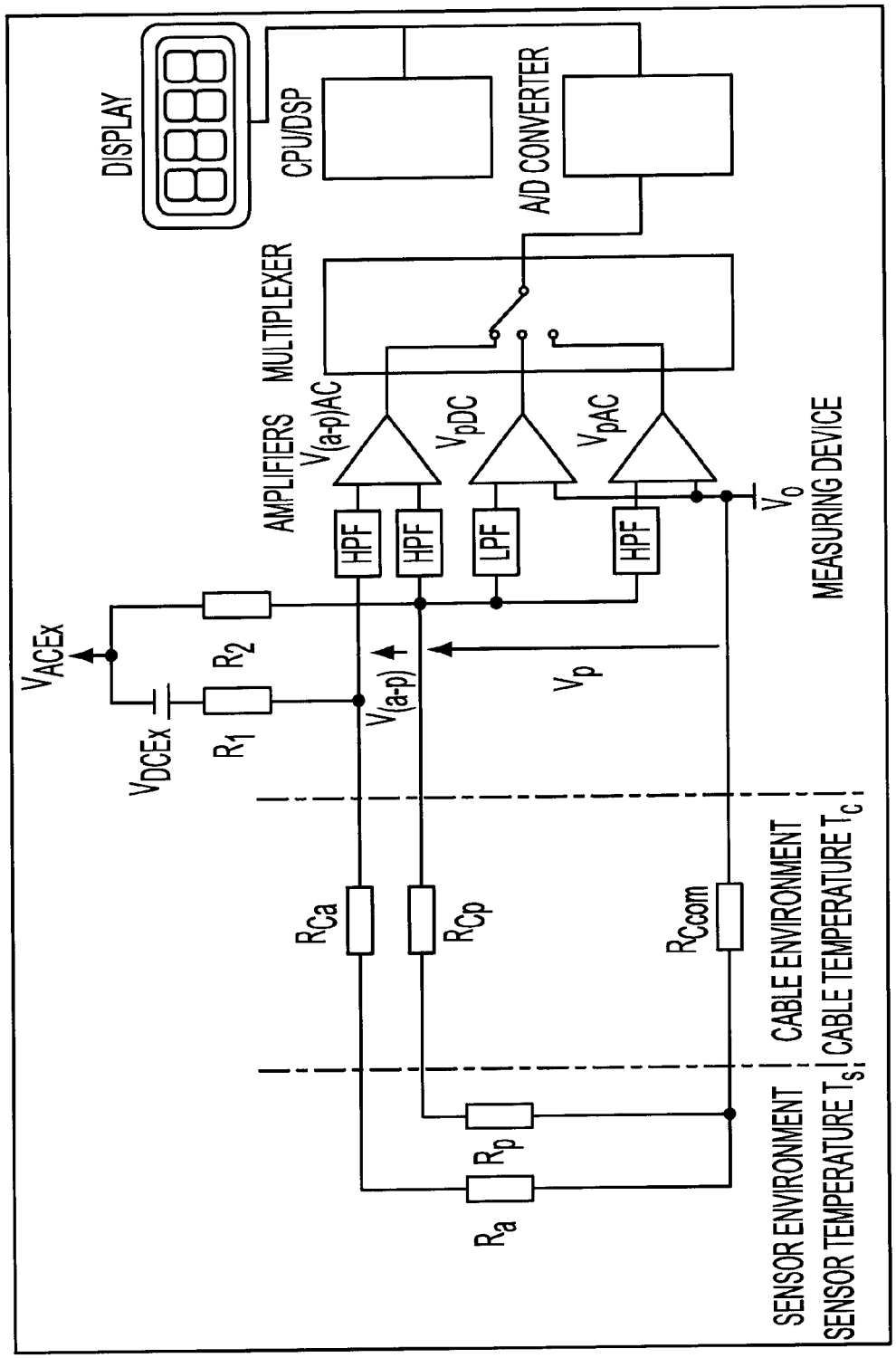
FIG. 5 is a simplified schematic circuit of the system used, with a second embodiment of the inventive feature.
Figure 6:
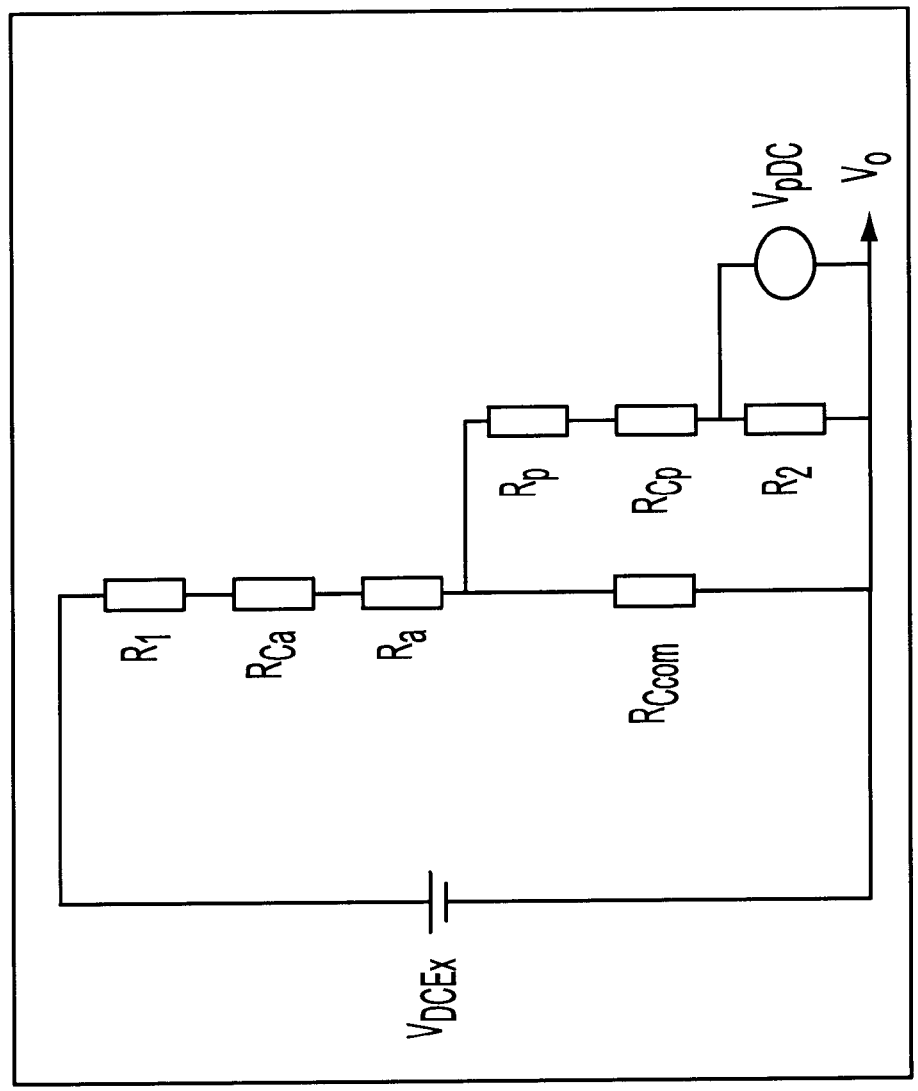
FIG. 6 shows an equivalent circuitry of the circuitry in FIG. 5 from a DC point of view.

The same algorithms as for the FIG. 5 can be used to achieve the cable resistance and the compensated temperature signal.

Figure 8:
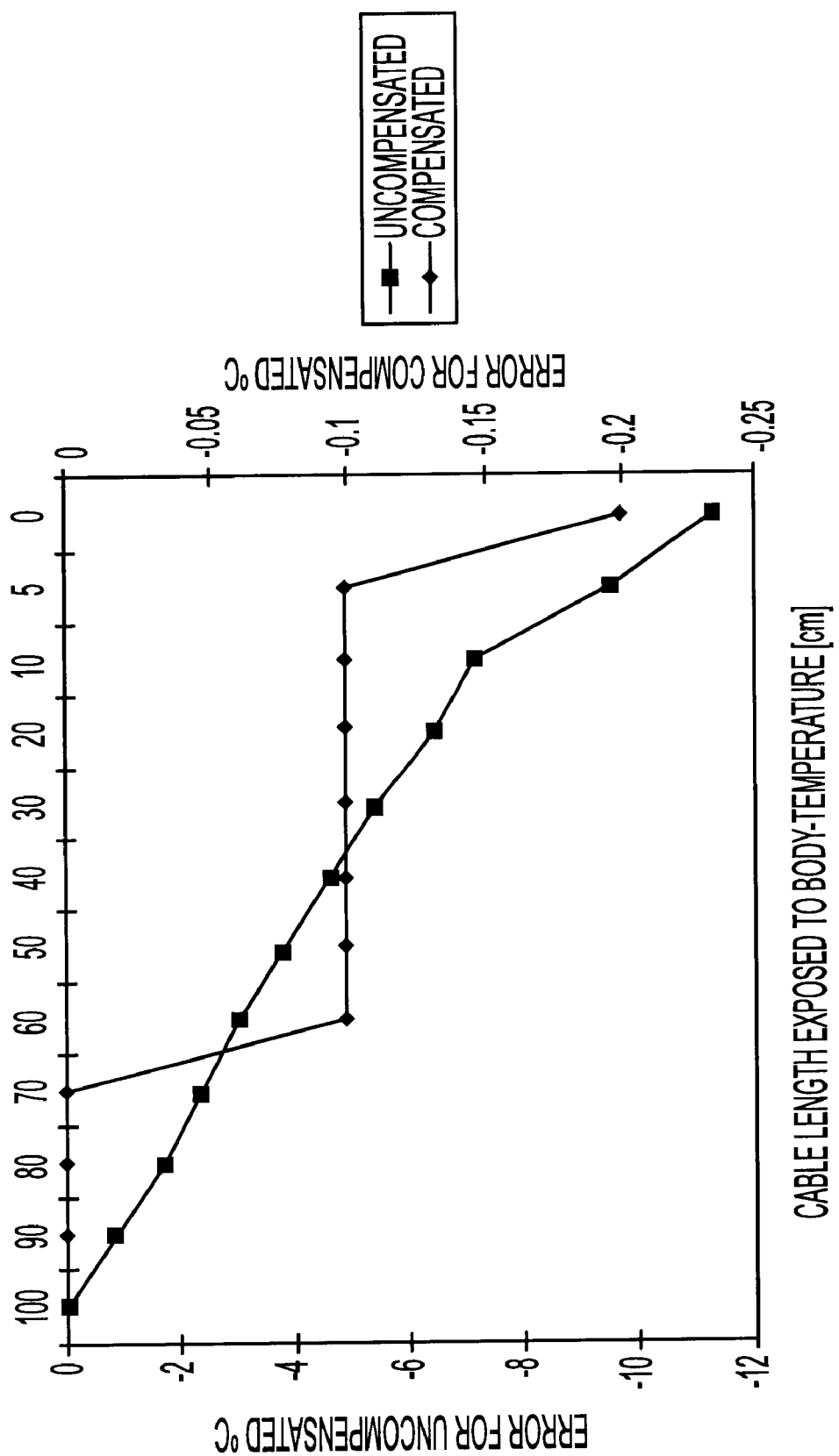
FIG. 8 is a graph showing the improvement in temperature readout with compensation according to the invention compared to without compensation.

In order to illustrate the effect of the compensation obtained the apparatus in accordance with invention the following example is given. The measurements shown in the diagram of FIG. 8 are achieved using the sensor disclosed in WO 97/27802. At the beginning of the experiment the sensor and 100 cm of the cables are immersed in a tank with 37° C. water, the rest of the cable (75 cm) and the measuring unit is located in the room temperature ≈20° C. Measured values $V_p$ of the uncompensated and compensated temperature signals are recorded for every 5 cm while the cable is removed from the tank. This experiment clearly demonstrates that the error of the uncompensated signal which is about 12° C. is decreased to less than 0.2° C. in the compensated signal.

What is claimed is:

1. A method of selectively measuring at least one of pressure and temperature in vivo, comprising the steps of:
   providing a pressure sensor having two piezoresistive elements, said piezoresistive elements being coupled to a control unit by cables having a temperature dependence affecting a signal obtained from said piezoresistive elements;
   providing excitation to said sensor to yield two different signals therefrom, such that at least a component of at least one of said signals is representative of cable resistance; and
   using said component representative of the cable resistance to compensate for the influence of said cable resistance on at least one of temperature and pressure signals.

2. The method according to claim 1, wherein the first piezoresistive element is part of one branch of a Wheatstone bridge, and the second piezoresistive element is part of another, branch of said Wheatstone bridge, and wherein the excitation comprise a first excitation of the entire bridge and a second excitation of only a branch of the bridge containing the first piezoresistive element.

3. The method according to claim 2, wherein the excitation is a DC voltage applied to the bridge.

4. The method according to claim 3, wherein the second excitation is carried out by switching off a branch containing the second piezoresistive element.

5. The method according to claim 4, wherein said second excitation is performed at a lower frequency than the first excitation.

6. The method according to claim 1, wherein the excitation comprises a composite excitation at two different frequencies.

7. The method according to claim 6, wherein said composite excitation comprises a DC voltage excitation and an AC voltage excitation.

8. The method according to claim 1, wherein the excitation voltage is up to 15 V.

9. The method according to claim 6, wherein an AC-component of a signal from the first piezoresistive element is obtained by high-pass filtering the signal before feeding it into an amplifier; the output from said amplifier is then fed into a multiplexer and further to an A/D converter where the signal is converted into digital data; said digital data is then read by a CPU/DSP which calculates a value of the signal as a pressure signal; an AC-component of a signal from the second piezoresistive element is obtained by high-pass filtering the signal before feeding it into an amplifier, the output from said amplifier is then fed into said multiplexer and further to said A/D converter where the signal is converted into digital data; said digital data is then read by the CPU/DSP which calculates a value as a temperature signal; and wherein a DC-component of a signal from the second piezoresistive element is low-pass filtered, and the filtered signal is fed into an amplifier, the output from said amplifier being fed into said multiplexer and further to said A/D converter where the signal is converted into digital data, this digital data being read by the CPU/DSP.

10. The method according to claim 1, wherein the sensor is mounted on a guide wire.

11. The method according to claim 1, wherein the sensor is mounted on a catheter.

12. A control unit suitable for processing signals from a sensor and guide wire assembly adapted to selectively measure at least one of pressure and temperature in vivo, said guide wire assembly comprising a pressure sensor and electrical conductors coupling said pressure sensor to said control unit, said pressure sensor having two piezoresistive elements, said assembly comprising parasitic resistances in said electrical conductors coupling said pressure sensor to the control unit, the control unit comprising:

means for selective excitation of said pressure sensor so as to yield two different signals therefrom;

means for selective registering of a component of one of said signals generated in response to excitation of said pressure sensor, said component being representative of said parasitic resistances; and means for compensating at least one of said different signals for influence of said parasitic resistances, by using said component representative of the parasitic resistances.

13. The control unit as claimed in claim 12, wherein the excitation means comprises a DC voltage source.

14. The control unit as claimed in claim 13, comprising a switch operable so as to enable cutting an excitation voltage to a piezoresistive element at a selected frequency.

15. The control unit as claimed in claim 14, further comprising a first and a second instrumental amplifier having inputs for receiving a pressure signal and a temperature signal respectively, and outputs delivering a processable out-signal, a multiplexer coupled to the outputs of said amplifiers, an A/D converter coupled to said multiplexer, and a control unit coupled to sequentially receive outputs from said A/D converter.

16. The control unit as claimed in claim 12, wherein the excitation means comprises a DC voltage source and an AC voltage source, whereby the DC and AC excitation voltages are superimposed on each other.

17. The control unit as claimed in claim 12, further comprising a first instrumental amplifier having high pass filter means coupled to its input, said input being coupled so as to receive a high frequency component of a pressure signal, a second instrumental amplifier having a low pass filter means coupled to its input, said input being coupled so as to receive a low frequency component of a temperature signal, and a third instrumental amplifier having a high pass filter means coupled to its input, said input being coupled so as to receive a high frequency component of said temperature signal and outputs delivering a processable out-signal, a multiplexer coupled to the outputs of said amplifiers, an A/D converter coupled to said multiplexer, and a control unit coupled to sequentially receive outputs from said A/D converter.

18. A system for measurement of at least one property inside a biological subject, the system comprising:

a sensor on an elongated member;

a cable connected to the sensor, the cable having a cable resistance; and a control unit, connected to the cable, that provides excitation to the sensor and cable to yield a signal representative of the cable resistance and that compensates the measurement of the property for influence of the cable resistance.

19. A system as set forth in claim 18, wherein the control unit provides two different excitation modes at two different periods of time, one of the two modes yielding the signal representative of the cable resistance.

20. A system as set forth in claim 18, wherein the control unit provides two different excitation frequencies, one of the two frequencies yielding the signal representative of the cable resistance.

21. A system as set forth in claim 18, wherein the elongated member is a guide wire.

22. A system as set forth in claim 18, wherein the elongated member is a catheter.

23. A system as set forth in claim 18, wherein the sensor is a pressure sensor.

24. A system as set forth in claim 18, wherein the sensor is a temperature sensor.

25. A system as set forth in claim 18, wherein the sensor is a pressure and temperature sensor.

26. A system as set forth in claim 18, wherein at least part of the cable is insertable inside the subject.

* * * * *